(12) United States Patent
Muller-Frischinger et al.

(10) Patent No.: US 8,263,687 B2
(45) Date of Patent: *Sep. 11, 2012

(54) COATING SYSTEM

(75) Inventors: Isabelle Muller-Frischinger, Riespach (FR); Michel Gianini, Delemont (CH); Jorg Volle, Selm-Bork (DE)

(73) Assignee: Huntsman International LLC, The Woodlands, TX (US)

( * ) Notice: Subject to any disclaimer, the term of this patent is extended or adjusted under 35 U.S.C. 154(b) by 771 days.

This patent is subject to a terminal disclaimer.

(21) Appl. No.: 11/722,501

(22) PCT Filed: Dec. 21, 2005

(86) PCT No.: PCT/EP2005/057055
§ 371 (c)(1),
(2), (4) Date: Jan. 22, 2010

(87) PCT Pub. No.: WO2006/067195
PCT Pub. Date: Jun. 29, 2006

(65) Prior Publication Data
US 2010/0210758 A1    Aug. 19, 2010

(30) Foreign Application Priority Data
Dec. 22, 2004  (EP) ................... 04106911

(51) Int. Cl.
C08L 63/00 (2006.01)
C08L 61/10 (2006.01)
C08L 61/12 (2006.01)
C08K 5/09 (2006.01)
C08G 59/56 (2006.01)
C08G 59/62 (2006.01)
B05D 1/00 (2006.01)
B05D 3/02 (2006.01)
B32B 27/26 (2006.01)
B32B 27/38 (2006.01)

(52) U.S. Cl. .................. 523/455; 427/386; 523/400
(58) Field of Classification Search .......... 427/386; 428/413, 418; 523/400, 455
See application file for complete search history.

(56) References Cited

U.S. PATENT DOCUMENTS

| | | | |
|---|---|---|---|
| 3,755,226 A * | 8/1973 | Christiansen et al. | 523/428 |
| 4,033,928 A * | 7/1977 | Randell et al. | 523/445 |
| 4,221,890 A | 9/1980 | Dimmick | |
| 4,389,515 A | 6/1983 | De La Mare et al. | |
| 4,397,998 A | 8/1983 | De La Mare et al. | |
| 4,689,390 A | 8/1987 | Suzuki et al. | |
| 4,866,133 A | 9/1989 | Andrews et al. | |
| 4,916,187 A | 4/1990 | Goel | |
| 4,977,214 A | 12/1990 | Bagga | |
| 5,198,146 A | 3/1993 | Shomer | |
| 5,243,014 A | 9/1993 | Shomer | |
| 6,074,702 A | 6/2000 | Robinson | |
| 6,465,601 B1 | 10/2002 | Wiesendanger et al. | |
| 6,649,729 B1 | 11/2003 | Scherzer et al. | |
| 6,716,930 B2 | 4/2004 | Yanagida et al. | |
| 6,750,300 B2 * | 6/2004 | Mahieu et al. | 525/523 |
| 8,003,737 B2 * | 8/2011 | Muller-Frischinger | 525/524 |

FOREIGN PATENT DOCUMENTS

| | | | |
|---|---|---|---|
| EP | 0253339 | | 1/1988 |
| JP | 2001164224 A | * | 6/2001 |
| JP | 2002114889 A | * | 4/2002 |

OTHER PUBLICATIONS

Machine translation of JP 2001164224 A, provided by the JPO website (no date).*
Machine translation of JP 2002114889 A, provided by the JPO website (no date).*
Lee & Neville, Handbook of Epoxy Resins, chapter 6-1 to 10-19, McGraw Hill Book Company, 1987.
Lee & Neville, Handbook of Epoxy Resins, chapter 2, pp. 257-307, 1967.
Directive 2002/72/EC, Commission of the European Communities, Aug. 6, 2002.
Directive 2004/19/EC, Commission of the European Communities, Mar. 1, 2004.

* cited by examiner

Primary Examiner — Michael J Feely

(57) ABSTRACT

A curable composition comprising
a) an epoxy resin containing on average more than one epoxy group per molecule, and
b) as curing agent a hybrid hardener, whereby said hardener is a blend of
b1) an aminic compound selected from aliphatic, cycloaliphatic, araliphatic amines, imidazoline group-containing amidoamines based on mono- or polybasic acids, adducts of said amines or amidoamines made from glycidyl compounds,
adducts of said amines or amidoamines with cyclic carbonates,
whereby said aminic compound contains, on average per molecule,
at least two reactive hydrogen atoms bound to nitrogen atoms, and
b2) a polyphenol novolac, and wherein the polyphenol novolac is used in an amount of from 30% to 45% by weight, based on the total weight of hardener blend comprising b1) and b2), useful for rapid setting and protective coatings and adhesives in application fields like civil engineering, marine, architectural and maintenance.

15 Claims, No Drawings

COATING SYSTEM

CROSS REFERENCE TO RELATED APPLICATIONS

This application is the National Phase of International Application PCT/EP2005/057055 filed Dec. 21, 2005 which designated the U.S. and which claims priority to European (EP) Pat. App. No. 04106911.3 filed Dec. 22, 2004. The noted applications are incorporated herein by reference.

This invention relates to rapid setting coating systems, based on epoxy resins and, as hardeners, blends of amines and novolac resins, for use as a protective coating for metallic and mineral substrates.

Curable compositions, based on glycidyl compounds and traditional polyamines or polyamidoamines, are widely used for ambient-cure-temperature epoxy systems in adhesives and coating application fields like civil engineering, marine, architectural and maintenance.

However, amines with high reactivity and fast cure rate become more and more indispensable for certain applications that require rapid return to service or shorter manufacture time. For instance, the manufacturing of ships or the relining of water pipelines with rapid return to service is application areas, where the traditional epoxy/amine chemistry does not fulfill, at the moment, the requirements of rapid cure, especially at low temperature. Otherwise compounds, which are commonly used to accelerate epoxy/amine systems—like tertiary amines, acids, hydroxylamines, and Mannich bases (described, for instance, in WO 00/015687)—do not permit to achieve such fast curing properties at low temperature.

Therefore, the present invention deals with new hybrid hardeners based on amines and phenolic resins which, in combination with epoxies, exhibit very fast cure rate, even at temperatures close to 0° C. Depending on the amines or blends of amines mixed with the phenolic resin, the final epoxy compositions show surprisingly acceptable viscosity ranges, with exceptional fast cure speed. It was, as well, surprising to observe, that the good chemical resistance of such cured epoxy systems was not altered by the introduction of phenolic resins into the epoxy/amine network. On the contrary, the chemical resistance of such systems was even improved toward chemicals like acetic acid 5% and 10%, compared to the neat epoxy/amine systems.

In the preferred embodiment of the invention, aliphatic, cycloaliphatic and araliphatic amines were used. Optionally, imidazoline-group-containing polyamidoamines, based on mono- or polybasic acids, adducts thereof and Mannich bases can be used, as well.

Furthermore, with regard to devices such as tanks or pipelines, coming into contact with food or drinkable water, further important aspects, besides fast curing and long term durability of the coating, are the toxicological properties of the cured epoxy systems employed as protective coatings. The migration of the constituents of the plastic materials and articles in food or potable water should not exceed certain limits. In this regard, "plastics" are understood as macromolecular compounds obtained by a process such as polymerization, polyaddition etc. Other substances or matter may be added to such macromolecular compounds. In any case, these substances should not migrate from the materials or articles into the foodstuffs, in quantities having a technological function in the final food. Considering for instance the UK legislation, the migration level of organic material for potable waterpipe (re)lining systems should not exceed 5 mg/liter (5 ppm) TOC (Total Organic Carbon). Also the migration of amines from the films should not exceed for such type of application certain limits depending on the amine used and specified in the directive of the individual countries.

As already mentioned, the present invention relates to rapid setting protective coating systems based on epoxy resins, useful, among other things, for internal (re)lining of pipes carrying potable water. Further possible applications include refurbishment of existing tanks, lines etc., which should return to service in a short time. In practice, this means that the curing should be achieved within a couple of hours, typically 2 to 5 hours, even at low temperatures, close to 0° C.

Accordingly, it is the object of this invention to provide fast epoxy systems which, while having a good cure speed at low temperature (as low as 3° C. for waterpipe relining), are toxicologically safe with low free amines content resulting from migration tests and deliver low TOC values.

Furthermore, such new hybrid hardeners could, as well, be useful for applications in which corrosion or chemical protection is required, such as tank lining. In this later case, conventional epoxy/amine systems exhibit poor resistance toward diluted acids. Only aromatic amines (e.g. diaminodiphenylmethane (DDM) and derivatives) show a noticeable resistance toward diluted acids, like acetic acid. However, such aromatic amines might well be banned from the market in the future, due to toxicity reasons. Therefore, the new hybrid hardeners have been shown to improve, in an exceptional way, the chemical resistance toward diluted acids like acetic acid, depending on the type of amine(s) used. To that respect, m-xylylenediamine (MXDA) based hybrid compositions show the best resistance toward such chemicals.

Another possible application area is marine, where many steel works on ships are exposed to salt, causing electrochemical corrosion and formation of rust. The anti-corrosive coating is generally applied to freshly sand-blasted steel and should be preferably cured and tacky-free after 24 h, even at temperatures as low as 0° C. Such novel class of amine/phenolic resin compositions offers both, rapid cure and improved resistance to corrosion, as can be seen from salt spray tests, performed according to the DIN 53167 and DIN 50021-SS methods. Compared to hardeners like phenalkamines, which are as well suitable for low temperature cure, such hybrid systems are much more rapid, while ensuring good corrosion resistance. Last but not least, the new hybrid hardeners are much less colored than phenalkamines, with the exception of natural alkylphenol cardanols having unsaturated double bonds and being more or less brownish colored raw materials.

A first object of the invention are curable compositions comprising
a) an epoxy resin containing on average more than one epoxy group per molecule, and
b) as curing agent a hybrid hardener, whereby said hardener is a blend of
b1) an aminic compound selected from aliphatic, cycloaliphatic, araliphatic amines, imidazoline group-containing amidoamines based on mono- or polybasic acids, adducts of said amines or amidoamines made from glycidyl compounds,
adducts of said amines or amidoamines made from cyclic carbonates,
whereby said aminic compound contains, on average per molecule,
at least two reactive hydrogen atoms bound to nitrogen atoms, and
b2) a polyphenol novolac, and wherein the polyphenol novolac is used in an amount of from 30% to 45% by weight, based on the total weight of the hardener blend b1) and b2).

The compositions according to the present invention are used for providing protective coatings and adhesives in application fields like civil engineering, marine architectural and maintenance.

The novolacs used in the instant invention can be prepared according to well-known processes, on reacting formaldehyde or paraformaldehyde with phenolic compounds—such as phenol, methylphenol (cresol), dimethylphenol (xylenol), other alkylphenols, those of bisphenol types, those of biphenyl-phenol or phenyl-phenol types and the like—on using, if required, a catalyst such as oxalic acid. The phenolic compound(s) as well as catalytic amounts of oxalic acid are generally placed in a vessel—with or without solvent or water—and formaldehyde, preferably paraformaldehyde, is added in portions. The volatile components are then removed by distillation under reduced pressure. The novolacs can be made from one or a mixture of different phenolic compounds. Such products are described, inter alia, in Houben-Weyl, $4^{th}$ edition, *Methoden der Organischen Chemie*, Vol. E 20, Makromolekulare Stoffe, Part 3, pages 1800-1806.

In a preferred embodiment of the invention the polyphenol novolac is a homopolymer resulting from the condensation of a phenolic compound of formula (I) or (II) with formaldehyde (paraformaldehyde) or a copolymer of different phenolic compounds of formula (I) and/or (II) with formaldehyde (paraformaldehyde):

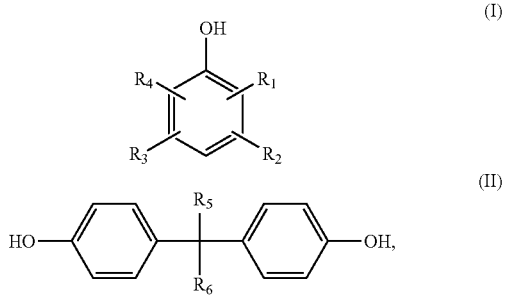

wherein in formula (I) and (II) $R_1$, $R_2$, $R_3$, $R_4$, independently of one another are H, branched or unbranched alkyl radicals containing 1 to 15 carbon atoms, and $R_5$, $R_6$ independently of each other represent H, $CH_3$, $CF_3$.

Preferred novolacs derived from compounds of formula (I) are those, wherein in formula (I) $R_1$, $R_2$, $R_3$, $R_4$ are either H (phenol), or alkylphenols, wherein, while the remaining radicals $R_1$ to $R_4$ are H, one or two of the radicals $R_1$ to $R_4$ are the radical —$CH_3$, or one of the radicals $R_1$ to $R_4$ is a tert-butyl radical, or one of the radicals $R_1$ to $R_4$ is a long-chain branched or unbranched alkyl radical containing 8 to 15 carbon atoms.

Preferred novolacs derived from compounds of formula (II) are those, wherein in formula (II) $R_5$, $R_6$ are both either —H or —$CH_3$.

According to this invention under polyphenol novolac being a copolymer of different phenolic compounds of formula (I) and/or (II) with formaldehyde is understood, that the novolac results from using a mixture of at least two different phenolic compounds when synthesizing the novolac.

The novolac, preferably derived from either a phenolic compound of formula (I) and/or (II), should be present in an amount of at least 30% by weight, preferably between 35 and 45% by weight based on the total weight of the hardener blend in order to get a liquid hardener composition at ambient conditions. In this respect, under ambient condition is understood normal room temperature of 20+/−5° C.

Similar compositions are known from WO 99/29757 and EP 0 266 306 A2. The WO 99/29757 discloses curable epoxy compositions wherein phenol novolacs are used in amounts being typical for acceleration, namely in weight percentages of 1 to 25%, based on amine hardener. EP 0 266 306 A2 discloses curable liquid epoxy compositions comprising a liquid epoxy resin and a solid latent curing agent to be dispersed into the resin, whereby said agent is a solid blend of a novolac and a polyamine in a ratio of from 50/50 to 80/20.

In another preferred embodiment of the invention, the polyphenol novolac comprises unreacted free phenolic compounds, preferably compounds of formula (I) and/or (II), in an amount of no more than 20%, preferably less than 15% and most preferably less than 10% by weight, based on the total weight of the hardener blend b1) and b2).

The novolacs prepared are statistical compositions, with a well defined polydispersity index. A narrow distribution of the polymer with a polymer index Ip~1.0 leads to polymer solutions within lower viscosity ranges. Therefore, in order to reduce the viscosity of the final system as much as possible, a polydispersity index Ip of around 1 is preferred. A good example of a commercially available phenol novolac is Supraplast® 3616 from Süd-West-Chemie GmbH, whose polydispersity index Mw/Mn lays around 1.39. The molecular weight of the phenolic novolac can be easily influenced on using a suitable excess of phenolic component(s) with respect to the amount of (para)formaldehyde.

The amine/novolac hybrid hardeners can for example be prepared by dissolving the novolac in the amine at approximately 90° C. under flow of nitrogen and under stirring for approximately half an hour.

The aminic compounds, which are blended with the polyphenol novolac resins and cured with the epoxy resins according to this invention are aliphatic, cycloaliphatic, araliphatic amines, imidazoline group-containing amidoamines based on mono- or polybasic acids, adducts of said amines or amidoamines made from glycidyl compounds, adducts of said amines or amidoamines made from cyclic carbonates, whereby said aminic compound contains, on average per molecule, at least two reactive hydrogen atoms bound to nitrogen atoms.

These compounds are part of the general state of the art and are described, inter alia, in Lee & Neville, "Handbook of Epoxy Resins", MC Grew Hill Book Company, 1987, chapter 6-1 to 10-19.

The amines used according to this invention are aliphatic, cycloaliphatic or araliphatic amines like: 1,2-diaminoethane (ethylenediamine (EDA)); 1,2-propanediamine; 1,3-propanediamine; 1,4-diaminobutane; 2,2-dimethyl-1,3-propanediamine (neopentanediamine); diethylaminopropylamine (DEAPA); 2-methyl-1,5-diaminopentane; 1,3-diaminopentane; 2,2,4-Trimethyl-1,6-diaminohexane; 2,4,4-Trimethyl-1,6-diaminohexane and mixtures thereof (TMD); 1-amino-3-aminomethyl-3,5,5-trimethylcyclohexane; 1,3-bis(aminomethyl)-cyclohexane; 1,2-bis(aminomethyl)cyclohexane; hexamethylenediamine (HMD); 1,2- and 1,4-Diaminocyclohexane (1,2-DACH and 1,4-DACH); bis(4-aminocyclohexyl)methane; bis(4-amino-3-methylcyclohexyl)methane; diethylenetriamine (DETA); 4-azaheptane-1,7-diamine; 1,11-diamino-3,6,9-trioxundecane; 1,8-diamino-3,6-dioxaoctane; 1,5-diamino-methyl-3-azapentane; 1,10-diamino-4,7-dioxadecane; Bis(3-aminopropyl)amine; 1,13-diamino-4,7-10 trioxamidecane; 4-aminomethyl-1,8-diaminooctane; 2-butyl-2-ethyl-1,5-diaminopentane; N,N-Bis-(3-aminopropyl)methylamine; triethylenetetramine (TETA); tetraethylenepentamine (TEPA); pentaethylenehexamine (PEHA); Bis(4-amino-3-methylcyclohexyl)methane; m-xylylenediamine (MXDA); 5-(aminomethyl)bicyclo[[2.2.1]hept-2-yl]methylamine (NBDA norbornanediamine); dimethyldipropylenetriamine; dimethylaminopropyl-aminopropylamine (DMAPAPA); 3-aminomethyl-3,5,5-trimethylcyclohexylamine (or isophoronediamine (IPD)); diaminodicyclohexylmethane (PACM); mixed polycyclic amines (MPGA) (e.g. Ancamine 2168); dimethyl-diaminodicyclohexylmethane (Laromin C260); 2,2-Bis(4-aminocyclohexyl)propane; bis aminomethyl-dicyclopentadiene (tricyclodecyldiamine (TCD)); imidazoline-group-containing polyaminoamides derived from aliphatic polyethylene polyamines and dimerized or trimerized fatty acids and adducts thereof made from glycidyl compounds.

Further, polyoxyalkylene polyamines, known as Jeffamine®, from Huntsman like D-230, D-400, D-2000, T-403, T-3000, T-5000, ED-600, ED-900, EDR148, and polyiminoalkylene polyamines, known as Polymin®, can be used, as well, to be blended with phenolic resins within the frame of the present invention.

Further suitable polyamines are 1,14-diamino-4,11-dioxatetradecane; dipropylenetriamine; 2-methyl-1,5-pentanediamine; N,N'-dicyclohexyl-1,6-hexanediamine; N,N'-dimethyl-1,3-diaminopropane; N,N'-diethyl-1,3-diaminopropane; N,N-dimethyl-1,3-diaminopropane; secondary polyoxypropylenedi- and triamine; 2,5-diamino-2,5-dimethylhexane; bis-(amino-methyl)tricyclopentadiene; 1,8-Diamino-p-menthane; Bis-(4-amino-3,5-dimethylcyclohexyl)methane; 1,3-Bis(aminomethyl)cyclohexane (1,3-BAC); dipentylamine. N-2-(aminoethyl)piperazine (N-AEP); N-3-(aminopropyl)piperazine; piperazine.

Preferably used as component b1) is an amine selected from aliphatic, cycloaliphatic, araliphatic amines. Preferred amines are selected from MXDA, IPD, TMD, 1,2-DACH, 1,3-BAC, DETA and diaminodicyclohexylmethane (PACM).

Using mixtures from several of the above mentioned amines are, as well, possible.

Furthermore, if the application is connected with foodstuff—as it is the case of drinking water pipelines—the aliphatic, cycloaliphatic or araliphatic amines, entering in the composition of the hybrid hardeners, should not infringe the regional regulations for plastics in contact with food or drinkable water. In Europe for instance, the polyamines, as well as all other components used in the new hybrid systems, have be found in the "positive list" published by the "Commission of the European Communities" in "*Directive* 2002/72/*EC*" of 6 Aug. 2002 and "*Directive* 2004/19/*EC*" of 1 Mar. 2004. Accordingly, amines found in said first draft "positive list" of the EU legislation—as it is the case of mixtures of 1,6-diamino-2,2,4-trimethylhexane and 1,6-diamino-2,4,4-trimethylhexane (TMD), xylylenediamine (MXDA), isophoronediamine (IPD) and blends thereof—can be used for potable water pipelines.

Suitable epoxy compounds, additionally used according to this invention for the preparation of the curable compositions, are commercially available products containing on average more than one epoxy group per molecule and are saturated or unsaturated linear or branched aliphatic, cycloaliphatic, aromatic or heterocyclic, and may bear substituents which do not materially interfere with the curing reaction.

Examples of epoxy resins suitable for use include those derived from mono- and/or polyhydric and/or polynuclear phenols, especially bisphenols and novolacs. They are diglycidylether of bisphenol A, diglycidylether of bisphenol F and polyglycidylethers of polyhydric phenol obtained from the reaction of phenol (or alkylphenols) and aldehydes such as formaldehyde.

Polyglycidylethers of alcohols, glycols or polyglycols, and polyglycidylesters of polycarboxylic acids can be used as well.

An extensive enumeration of these compounds is to be found in the compendium "Epoxidverbindungen und Epoxidharze" by A. M. Paquin, Springer Verlag, Berlin, 1958, chapter IV, and in Lee & Neville, "Handbook of Epoxy Resins", 1967, chapter 2, pages 257-307.

It is also possible to use mixtures of two or more than two different epoxy compounds.

The epoxy compounds can be liquid in particular liquid bisphenols or liquid novolacs. Also semi-solid or solid resins, especially those of type 1, can be used. Some commercially available solid resins of type 1 are available from Huntsman under the trade names Araldite® GT 7071 and GT 6071. In case of using semi-solid or solid resins a solvent is needed to dissolve the epoxy resin and to reduce the viscosity in such a way that the product can be sprayed, as it is the case in marine applications. Additionally also epoxy compounds derived from advancement reactions, for example the advancement of novolacs with bisphenol A could be used as well.

According to the invention, It is preferred to select compound a) from diglycidylether of bisphenol A, diglycidylether of bisphenol F, polyglycidylether of polyhydric phenol or cresol novolacs, mono- or polyglycidylether of mono- or polyhydric cycloaliphatic alcohols, mono- or polyglycidylether of mono- or polyhydric aliphatic alcohols.

Blends of epoxy resins with so-called reactive diluents, e.g. glycidyl ethers of: mono- or polyhydric phenols, mono- or polyhydric aliphatic alcohols, mono- or polyhydric cycloaliphatic alcohols, can be used as well. Some suitable examples are: cresylglycidylether, p-tert.-butyl-phenylglycidylether, n-dodecyl-/n-tetradecylglycidylether, 1,4-butanedioldyglycidylether, 1,6-hexanediol-diglycidylether, trimethyloipropanetriglycidylether, polyglycidylether like polyoxypropylenediglycidylether, cyclohexane-dimethanol-diglycidylether, glycidylester of neodecanoic acid and of cyclohexanedicarboxylic acid.

If necessary, the viscosity of the epoxy resins can be further reduced by adding such reactive diluents and should only be used in reasonable amounts so that the diluents may not adversely affect the end-properties of the thermoset. The epoxy resins mentioned as examples can be used both for the curable compositions and for the preparation of the amine-epoxy adducts, that may be blended with the phenolic novolac resin.

In a preferred embodiment of the invention blends of the epoxy compound a) with reactive diluents are used, by pre-mixing the epoxy resin with at least one reactive diluent.

Also the already mentioned cyclic carbonates can be used not only for the preparation of amine adducts, however they can also be used in combination with epoxies for the curable composition. These carbonates can be of various types, for instance the reaction product of alkylene oxide compounds with carbon dioxide, or based on the reaction product of glycidyl compounds with carbon dioxide. Preferred compounds are monofunctional cyclic carbonates like $C_2$-$C_4$-alkylene carbonates.

In another preferred embodiment of the invention, a combination of an epoxy resin with propylene carbonate reduces significantly the viscosity of the formulation and therefore the system needs less solvent to be spray applicable. This is compliant with the environmental legislation on VOC's, which increasingly becomes strict and affords for high solid applications (low-VOC paints). The said cyclic carbonates could be added at different weight ratios but should not adversely affect the cure speed and the end properties of the thermosets. The cyclic carbonates and the epoxy resin to be cured can simply be mixed together. A suitable ratio between epoxy resin and carbonate in weight percent is from 75:25 to 99:1, preferably from 80:20 to 99:1 and most preferably 85:15 to 98:2.

In another preferred embodiment a preliminary modification with cyclic carbonate (the pre-reaction of an amine or a blend of amines with cyclic carbonate) is performed. This has the advantage to improve somewhat the intercoat-adhesion. However the modification with cyclic carbonate is linked to an increase of the viscosity of the final hybrid hardener. Preferably the preliminary modification of the amine is made with less than 30 wt % of cyclic carbonate and most preferably with less than 25 wt % based on modified hardener. Suitable and preferred amines used for this embodiment are identical to those mentioned before.

Hybrid hardeners and epoxy compounds are preferably used in about equivalent amounts, i.e. based on active hydrogen's bound to amino nitrogen atoms and reactive epoxy groups. However, it is also possible to use the hybrid hardener or the glycidyl component in more or less than the equivalent amount. The amounts used depend on the desired final properties of the reaction product as known by the skilled persons in the art.

The epoxy resin composition can optionally further include other additives selected for example from flow control additives, antifoaming agents, anti-sag agents, pigments, reinforcing agents, fillers, elastomers, stabilizers, extenders, plasticizers, flame retardants, accelerators, colorants, fibrous substances, thixotropic agents, anti-corrosive pigments and solvents.

Obviously, only those of said additives may be employed, provided that they have no resulting adverse effects on drinking water or on food quality.

As mentioned, accelerators in catalytic amounts for epoxy/amine reactions can be used in addition to the new amine/polyphenol hybrid hardeners. Suitable examples are for instance Mannich base type accelerators like Accelerators 2950 and 960-1 from Huntsman Advanced Materials, tertiary amines like benzyldimethylamine (BDMA), metal salts like hydroxides and nitrates most known those of group I and group II metals such as calcium, lithium etc. as described in EP 0 083 813 A1 and EP 0 471 988 A1, or acids like salicylic acid can be added as well. In a preferred embodiment of the invention, the accelerator is salicylic acid. The amount of accelerator is from 0.1 to 10, preferably from 0.3 to 5, more preferably from 0.5 to 3% per weight based on the total weight of amine/novolac/accelerator.

The quantity of phenolic resin depends principally on the type of amine or mixture of amines as well on the type of phenolic resin used to prepare the hybrid hardener and on the targeted viscosity/properties for a given application. To that respect, the viscosity of the hybrid hardeners should be preferably lower than 20 000 mPa·s at ambient temperatures. Only in the case of high hardener blend viscosities or even semi solid compositions having high dynamic shear viscosities, it is desirable to add a solvent to the hardener blend in order to reduce the viscosity of the final formulation to make said formulation spray or brush applicable. Standard solvents, like xylene/butanol mixtures or pure alcohols like methoxypropanol are commonly used. But organic solvents can be used only in certain cases, as they are not recommended, for instance, in potable water pipe re(lining) or wine tank lining applications.

In the case of the instant invention, it is appropriate to speak of amine/novolac hybrid hardeners, as it has surprisingly been found that the most efficient ratio between amine/novolac, in terms of curing rate and chemical resistance, is between 70/30 and 55/45, preferably between 65/35 and 55/45. Surprisingly, the amine/novolac blend remains liquid, even at ratios around 60/40. For example if Supraplast 3616 is used as phenolic resin, the best ratio of the amine/novolac blends is found to be 60/40 in the case of the amines trimethylhexamethylenediamine (TMD) or m-xylylenediamine (MXDA).

As mentioned before, the proportions of amine/polyphenol novolac can be varied, depending on the desired properties in terms of viscosity, curing rate, chemical resistance and corrosion protection. It was surprisingly observed, that the chemical resistance toward aggressive chemicals like a 5 or 10 wt % aqueous solution of acetic acid could be significantly improved by using a concentration of at least 30 wt %, preferably from 35 to 45 wt % polyphenol novolac based on the total weight of the hybrid hardener comprising the amine and polyphenol novolac. This is especially surprising due to the reduced network density of the combination of the amine with polyphenol novolac.

The inventive curable compositions can be cured at a temperature within the range of from −40° C., preferably from about −10° C., to about 150° C. for a sufficient time to fully cure the epoxy resin. For standard ambient cure applications, the composition is preferably cured at a temperature from about −5° C. to about 50° C.

A further inventive object is a cured material, obtained from curing an inventive composition.

The invention further provides curable compositions for coating, adhesively bonding, or as flooring, casting, tooling or encapsulating materials, to name a few applications. The epoxy compositions have particularly good applicability for coatings, especially when combined with pigments. The epoxy compositions using the novel hybrid hardeners described above can for example advantageously be combined with an anti-corrosive pigment like zinc phosphate or zinc powder to produce paint formulations having high corrosion resistance for marine and heavy duty applications. Furthermore the compositions can also include pigments like iron oxide and titanium dioxide and a filler like barium sulfate, to give protective coatings for wine tanks and pipes. The resulting formulations can be applied on at least one surface of the substrate to be coated in conventional manner by spraying, roller coating, brushing etc. or with special equipments like a twin-feed spray equipment and the like, depending on the gel time of the system.

A further object of the instant invention is the use of a hardener blend b) as curing agent, whereby said hardener is a blend of b1) an amine selected from aliphatic, cycloaliphatic, araliphatic amines or imidazoline group-containing amidoamines based on mono- or polybasic acids or their adducts made from glycidyl compounds or cyclic carbonates, which contain, on average, more than two reactive active hydrogen atoms bound to amino nitrogen atoms per molecule, and b2) a polyphenol novolac, and wherein the polyphenol novolac is used in an amount of 30-45 wt %, preferably from 35 to 45 wt %, based on the total weight of hardener blend comprising components b1) and b2).

Suitable and preferred amines, cyclic carbonates and polyphenol novolacs which can be used for this object are identical to those mentioned before with regard to curable epoxy resin compositions. Further accelerators can be used in addition to the amine/polyphenol novolac hardener blends. Suitable and preferred catalysts and appropriate amounts are those as already mentioned before.

EXAMPLES

A) Cure Properties of Hybrid Hardeners Based on Blends of Amine and Novolac

The following hybrid hardeners have been prepared by dissolving the novolac resin Supraplast 3616 in different amines or amine mixtures at the temperature of 80° C.; the characteristics of the hybrid hardeners are given below in table 1.

TABLE 1

Hybrid hardener compositions with different ratios of amine and polyphenolic resin

| | Blend | | |
|---|---|---|---|
| | A | B | C |
| MXDA [1] | 30.0 | 59.0 | — |
| TMD [2] | 30.0 | — | 60.0 |
| Novolac Supraplast 3616 [3] | 40.0 | 41.0 | 40.0 |
| Viscosity hardener at 25° C. [4] | 7100* | 7000* | 7700* |

[1] MXDA = m-xylylenediamine in wt %;
[2] TMD = Trimethylhexamethylenediamine (isomer mixture see description before) in wt %,
[3] Novolac resin Supraplast 3616 in wt % purchased at Sud-West-Chemie GmbH Neu-Ulm with following characteristics Mn = 341, Mw = 474, Ip = 1.39 determined by using GPC-RI: Columns: 3 × Mixed-C; eluant: THF at 1 ml/min, Polystyrene calibration and it contains less than 0.8% free phenol;
[4] Viscosity of amine/novolac blend was determined at 25° C. using a CAP 2000 viscosimeter with cone 6 at 500 rpm (ISO 3219).
*an average value resulting from the repetition of several synthesis examples.

The table 2 below gives the cure properties of different epoxy systems comprising different blends of amine/novolac resin cured at both temperatures 0° C. and 5° C.

TABLE 2

Cure properties of the hybrid hardeners compared to neat amines MXDA and TMD

| Formulation | 1 | 2 | 3 | Comp. 1 | Comp. 2 |
|---|---|---|---|---|---|
| Epoxy resin [1] | 73.86 | 75.03 | 72.20 | 84.56 | 81.23 |
| amine/novolac blend A) [2] | 26.14 | — | — | — | — |
| amine/novolac blend B) [2] | — | 24.97 | — | — | — |
| amine/novolac blend C) [2] | — | — | 27.80 | — | — |
| MXDA | — | — | — | 15.44 | — |
| TMD | — | — | — | — | 18.77 |
| Viscosity of formulation at 25° C. [3] | 9400 | 9800 | 11000 | 660 | 480 |
| Full cure at 0° C. (hours) [4] | 3.5 | 3.5 | 3.0 | 11.5 | 13 |
| Dust free at 0° C. (hours) [5] | 4.5 | 4.0 | 4.0 | 4.0 | >24 |
| Full cure at 5° C. (hours) [4] | 3.0 | 2.5 | 3.0 | 11.0 | 11 |
| Dust free at 5° C. (hours) [5] | 3.5 | 2.5 | 2.0 | 2.5 | >24 |

Coating thickness measured on glass is between 250-300 μm.
[1] PY302-2 with Epoxy equivalent weight of EEW 173 in wt %;
[2] in wt %;
[3] Viscosity of the formulation was determined at 25° C. using a CAP 2000 viscosimeter (ISO 3219) with cone 6 at 500 rpm for formulations 1, 2 and 3 and with cone 3 at 500 rpm for comparatives 1 and 2;
[4] [5] the cure times were measured on Landolt equipment using glass sheets coated with the above formulations. To determine the full cure, a needle is continuously moving forward on the coated glass during exactly 24 h; the full cure is determined by measuring the distance/time where the needle, penetrating the film, comes out from the film. To determine dust free time, sand is continuously added to the coating surface; the dust free time is measured by removing the sand from the coating surface and measuring the distance/time where sand sticks on the coating surface.

The results for the inventive compositions, especially if compared with the two comparative (=Comp.) examples given in table 2, show excellent cure times for both measurement methods full cure and dust free even at 0° C., which is very exceptional for epoxy systems.

The table 3 below gives the hardness in Shore D in function of the cure times at different cure temperatures and relative air humidity conditions for the formulations 1, 2 and 3 as listed in table 2.

TABLE 3

Hardness in Shore D values for some coatings in function of the cure time and under different relative air humidity conditions.

| | Shore D values [1] for formulation | | |
|---|---|---|---|
| | 1 | 2 | 3 |
| after 1 day (d) at 0° C. | 45 | 30 | 70 |
| 7 d at 0° C. | 70 | 70 | 75 |
| 21 d at 0° C. | 70 | 75 | 76 |
| after 1 day (d) at 5° C. | 65 | 65 | 70 |
| 7 d at 5° C. | 75 | 75 | 75 |
| 21 d at 5° C. | 75 | 80 | 80 |
| after 1 day (d) at 23° C./50% rel. air humidity | 79 | 81 | 80 |
| 7 d at 23° C./50% rel. air humidity | 79 | 81 | 80 |
| 21 d at 23° C./50% rel. air humidity | 79 | 81 | 80 |
| after 1 day (d) at 23° C./100% rel. air humidity | 80 | 81 | 78 |
| 7 d at 23° C./100% rel. air humidity | 80 | 81 | 78 |
| 21 d at 23° C./100% rel. air humidity | 80 | 81 | 80 |

[1] Shore hardness was measured using a 4 mm thick sample following the Shore D hardness test ISO 868 & DIN 53505 (method A/D)

The results of table 3 show that all three formulations exhibit very high Shore D hardness after one day cure at 5° C. with values above 60, which shows the exceptional fast cure rate of such systems.

B) Cure Properties of Hybrid Hardeners Based on the Amine MXDA and Different Types of Novolacs: Bisphenol a Novolac, Bisphenol F Novolac The following novolacs have been prepared according to well-known processes, on reacting formaldehyde or paraformaldehyde with phenolic compound(s)—such as bisphenol A and bisphenol F—using a catalyst such as oxalic acid.

Example of Synthesis of a Novolac from Bisphenol A 114.15 g (0.5 mol) of bisphenol A, 34.5 g of an aqueous 37% formaldehyde solution and 2.02 g oxalic acid are mixed together and heated up to 130° C. under stirring and flow of nitrogen within 25 min, and kept at this temperature for 1 h 30 min. After this time, the formed water is removed by distillation under reduced pressure of 50 mbar at 170° C. for 2 h 20 min and finally the temperature is increased to 190° C. to discharge the formed polymer, which characteristics are given in table 4.

Example of Preparing a Novolac from Bisphenol F 100 g (0.5 mol) of bisphenol F, 30.44 g of an aqueous 37% formaldehyde solution and 2.02 g oxalic acid are mixed together and heated up to 130° C. under stirring and flow of nitrogen within 20 min, and kept at this temperature for 2 h 30 min. After this time, the formed water is removed by distillation under reduced pressure of 30 mbar at 170° C. for 2 h 35 min and the formed polymer is finally discharged at such temperature of 170° C., which characteristics are given in table 4.

TABLE 4

GPC characteristics of different synthesized novolacs

|  | Novolacs from: | |
|---|---|---|
|  | Bisphenol A | Bisphenol F |
| Mn [1] | 1062 | 1075 |
| Mw [1] | 2631 | 3066 |
| Ip [1] | 2.48 | 2.85 |
| Remaining free monomer content (wt %) [2] | 15.0 | 11.8 |
| Tg (° C.) [3] | 99.3 | 74.5 |

[1] Mn and Mw determined using GPC-RI with Polystyrene calibration;
[2] determined by HPLC with external standard;
[3] Glass transition temperature was determined by DSC using a heat rate of 10° C./min and was taken after the 1st scan at the inflection point.

The following hybrid hardeners have been prepared by dissolving the above mentioned novolac resins in MXDA at a temperature of 100° C.; the characteristics of the hybrid hardener blends are given below in table 5.

TABLE 5

Hybrid hardener compositions of amine MXDA mixed with different novolac resins

|  | Blend | |
|---|---|---|
|  | D | E |
| MXDA [1] | 70 | 70 |
| Novolac from bisphenol A (wt %) | 30 | — |
| Novolac from bisphenol F (wt %) | — | 30 |
| Viscosity at 25° C. [2] | 2300 | 5600 |

[1] MXDA = m-xylylenediamine in wt %,
[2] Viscosity of amine/novolac blend was determined at 25° C. using a CAP 2000 viscosimeter at 500 rpm and with cone 6

The cure properties of hybrid hardeners based on other types of novolacs were determined as well in table 6. The combinations of the novolac from bisphenol A with MXDA (hardener blend D) and the novolac from bisphenol F with MXDA (hardener blend E) both improve the cure speed of the system but are less efficient than the combination of the phenol based novolac Supraplast 3616 with MXDA.

TABLE 6

Cure properties of the hybrid amine/novolac hardeners from bisphenol A or bisphenol F

|  | Formulation | | |
|---|---|---|---|
|  | 4 | 5 | Comp. 3 |
| Epoxy resin [1] | 79.32 | 79.32 | 84.56 |
| amine/novolac blend D) [2] | 20.68 | — | — |
| amine/novolac blend E) [2] | — | 20.68 | — |
| MXDA [3] | — | — | 15.44 |
| Viscosity of formulation at 25° C. [4] | 4500 | 5100 | 920 |
| Full cure at 0° C. (hours) [5] | 8.5 | 9.0 | 11.0 |
| Dust free at 0° C. (hours) [6] | >24 | >24 h | 4.0 |
| Full cure at 5° C. (hours) [5] | 6 | 8.5 | 10.5 |
| Dust free at 5° C. (hours) [6] | 3.5 | 6.5 | 3.0 |

[1] GY 250 with Epoxy equivalent weight of EEW 186 in wt %;
[2] in wt %;
[3] MXDA = m-xylylenediamine in wt %;
[4] Viscosity of the formulation was determined at 25° C. using a CAP 2000 viscosimeter (ISO 3219) with cone 6 at 500 rpm for formulation 4, 5 and with cone 3 at 500 rpm for comparative 3;
[5,6] the cure times were measured on Landolt equipment using glass sheets coated with the above formulations (see described method before). Coating thickness measured on glass was between 250-300 μm.

C) Adduction of an Amine Mixture MXDA/TMD with Propylene Carbonate and Further Modification with Polyphenol (Supraplast 3616)

An amine mixture of MXDA/TMD with a ratio of 90/10 was modified with propylene carbonate following the procedure below:

76.50 g (0.562 mol) of amine meta-xylylene diamine (MXDA) and 8.50 g (0.054 mol) trimethylhexamethylenediamine isomer mixture (TMD) was heated up to 80° C. and 15 g propylene carbonate (0.147 mol) is then added to the reaction mixture within 30 minutes. The reaction mixture is then additionally heated during 3h at 80° C. The final amine adduct hardener F has a viscosity of less than 100 mPa·s (measured by CAP 2000, cone 3, 900 rpm). Then 70 g MXDA/TMD-propylene carbonate adduct F was mixed with 30 g Supraplast 3616 at 80° C. to give finally a hybrid hardener G in table 7. This hybrid hardener was then formulated and tested in combination with an epoxy resin (Araldite GY 250) and the resulting cure properties are given in table 8. It is noteworthy to say at this stage that it is also possible to add the propylene carbonate directly to the epoxy component, the reaction between the carbonate-amine happening during the curing stage. The cure properties of both types of formulation are given in table 8.

TABLE 7

Viscosity of hybrid hardener [(MXDA/TMD) propylene carbonate] adduct further blended with Supraplast 3616 compared to hybrid hardener MXDA/TMD/Supraplast 3616

|  | Hardener blend | |
|---|---|---|
|  | G | H |
| Hardener F [1] | 70 | — |
| MXDA [2] | — | 58.5 |
| TMD [3] | — | 6.5 |
| Novolac Supraplast 3616 [4] | 30 | 35 |
| Viscosity of hardener at 25° C. [5] | 9400 | 1100 |

[1] in wt %;
[2] MXDA = m-xylylenediamine in wt %;
[3] TMD = Trimethylhexamethylenediamine (isomer mixture see description before) in wt %,
[4] in wt %;
[5] Viscosity of amine/novolac blend was determined at 25° C. using a CAP 2000 viscosimeter at 500 rpm and with cone 6.

The results with regard to viscosities of the formulations at 25° C. show that the premixing of the epoxy resin with propylene carbonate reduces significantly the viscosity of an inventive formulation, see examples 8 and 10 in comparison to example 12 with the unmodified hybrid hardener H. To the contrary, a preliminary modification of the amine with propylene carbonate (example 6 with the pre-reacted hardener G) increases the viscosity of the final formulation but leads to approximately the same curing time than for unmodified hardener using such concentration of propylene carbonate and in absence of solvent. The advantage of the modification is however, a sensible improvement of intercoat-adhesion observed at such level of modification or even at a superior concentration of propylene carbonate.

In general the cure times are slightly altered by the modification of the system using a concentration below 5 wt % of propylene carbonate and more visible in the case of a preliminary modification of the amine and addition of a solvent, whereby an increase of cure time is always observed; however such type of systems with hybrid hardeners are still considered to be very fast curing if compared to neat amine systems.

At higher concentrations of propylene carbonate (above 5 wt % of propylene carbonate based on the total mixture GY250/propylene carbonate) the cure times are more affected by such modification.

The modification by adding a monofunctional cyclic carbonate able to react with the amine component reduces somewhat the crosslinking density of the system, which in turn could lead to a reduced chemical resistance.

TABLE 8

Properties of a preliminary modified (pre-reacted) hybrid hardener MXDA/TMD with propylene carbonate and further blended with Supraplast 3616 compared to an unmodified hybrid hardener MXDA/TMD/Supraplast 3616 combined with GY 250 or a mixture of GY 250 with propylene carbonate.

|  | 6 | 7 | 8 | 9 | 10 | 11 | 12 | 13 |
|---|---|---|---|---|---|---|---|---|
| Formulation |  |  |  |  |  |  |  |  |
| Epoxy resin mixture: Araldite GY 250/propylene carbonate [97.3/2.7] [1)] | — | — | 78.19 | 78.19 | — | — | — | — |
| Epoxy resin mixture: Araldite GY 250/propylene carbonate [95/5] [1)] | — | — | — | — | 74.24 | 74.24 | — | — |
| Ep resin Araldite GY 250 [1)] | 75.12 | 75.12 | — | — | — | — | 77.81 | 77.81 |
| Hardener G [1)] | 24.88 | 24.88 | — | — | — | — | — | — |
| Hardener H [1)] | — | — | 21.81 | 21.81 | 22.76 | 22.76 | 22.19 | 22.19 |
| Solvent mixture 1-butanol:xylene 4:1 [1)] | — | 8.40 | — | 6.00 | — | 5.60 | — | 8.32 |
| Viscosity of formulation at 25° C. [2)] | 12300 [*)] | 1020 | 4300 | 1040 | 3200 | 1030 | 7600 | 1280 |
| Cure properties |  |  |  |  |  |  |  |  |
| Full cure at 0° C. (hours) [3)] | 4 | 10 | 5 | 8 | 5 | 8 | 4 | 6 |
| Dust free at 0° C. (hours) [4)] | 4 | 9 | 5 | 6 | 5 | 7 | 4 | 6 |
| Full cure at 5° C. (hours) [3)] | 3 | 7 | 4 | 6 | 3 | 6 | 3 | 5 |
| Dust free at 5° C. (hours) [4)] | 2.5 | 3.5 | 4 | 2 | 5 | 2 | 3 | 1.5 |
| Flexibility test via: |  |  |  |  |  |  |  |  |
| Mandrel test/15 mm [5)]: |  |  |  |  |  |  |  |  |
| After 1 week cure at 23° C. | 20° | 30° | 25° | 30° | 20° | 25° | 15° | 30° |
| After 2 weeks cure/23° C. | 20° | 35° | 30° | 30° | 25° | 35° | 25° | 50° |
| After 1 month cure/23° C. | 30° | 50° | 30° | 30° | 35° | 45° | 35° | 70° |

[*)] Being very reactive, it was difficult to measure the viscosity. Coating thickness measured on glass was between 150-200 μm.
[1)] in wt %,
[2)] Viscosity of amine/novolac blend was determined at 25° C. using a CAP 2000 viscosimeter at 500 rpm and with cone 6;
[3) 4)] the cure times were measured on Landolt equipment using glass sheets coated with the above formulations (see described method before).
[5)] Mandrel bending test according to ISO 1519/73

D) Application Water Re(Lining) Systems Migration Tests of Hybrid Hardeners

The TOC (Total Organic Carbon) results were obtained using, for the preparation of the sample, an internal method of cure and simulation of pipe cleaning. The results were obtained by using the following method of preparation:

The bottom of a beaker glass having a diameter of 8 cm is cleaned with acetone and deionised water. A 1 mm thick material is casted on the bottom of the becher glass; the material is allowed to cure during 3 hours at 3° C. and after this time the surface of the material is cleaned with a stream of water during 1 hour to simulate the cleaning of the pipe. The material is then extracted with 200 ml deionised water during 24 hours and the extract is analyzed for its TOC content (using a method of Norm ISO 8245:1999). Also the free amine content in the extract was determined by HPLC and GC-MS. The final migration results are given in table 9.

TABLE 9

TOC and free amine migration results

| Formulation | 1 | 2 | 3 | LOD [*)] | DWL [**)] |
|---|---|---|---|---|---|
| TOC [ppm] | 0.18 | 0.58 | 0.57 | 0.01 [***)] | — |
| TMD [μg/l] | <60 | Nd | <60 | 60 [****)] | 250 |
| MXDA [μg/l] | <5 | <5 | Nd | 5 [*****)] | 2.5 |

Note:
The actual measured values are between 0.38 and 0.77. Although the deionisized water itself has already a TOC of 0.2 ppm.
[*)] LOD: limit of detection;
[**)] DWL (Drink Water Limits): Provisional limits of the positive list for drinking water proposed by the German legislation and also by the Commission of the European Communities
[***)] TOC: 0.01 ppm is the limit of detection;
[****)] TMD: 60 [μg/l or ppb] is the limit of detection obtained by HPLC with preliminary derivatization of the amine TMD;
[*****)] MXDA: [μg/l or ppb] is the limit of detection obtained by GC-MS with preliminary derivatization of the amine MXDA;
Nd: means not determined.

These results show finally that even if the systems are cured at temperatures as low as 3° C., they deliver very low concentrations of free amines after extraction with water, which are below the limits indicated in the European positive list of assessed substances used in the manufacture of plastics for food. Therefore these hardeners could also fulfill the requirements of migration levels specified in the future European Directive, and thus also in the individual countries, for drinking water.

E) Chemical Resistance of Hybrid Hardener Blends Combined with Epoxy Resin

The chemical resistance was tested on coatings applied approximately 500 microns thick on sand-blasted steel panels Sa $2^{1/2}$, which were cured for 10 days at 23° C. and 50% rh.

The chemical resistances of inventive hybrid hardener blends were compared to those of unmodified amines, for instance TMD or MXDA, and also to those of amine/novolac resin mixtures being at the superior limit of the compositions claimed in the patent WO 99/29757 for instance at the ratio amine/novolac resin 75/25.

First the results for the chemical resistance of pure amines like TMD and MXDA are given in tables 10 and 11 below. Both amines do not show at all resistance toward aqueous solution of acetic acid 5 and 10 wt %, the films being destroyed in less than 3 days once in contact with such aggressive chemicals.

TABLE 10

Chemical resistance of the neat system MXDA/Araldite GY250 (unmodified system)

| Epoxid/Hardener | Araldite GY250: MXDA: | | | | 84.56 parts/ 15.44 parts | | | | |
|---|---|---|---|---|---|---|---|---|---|
| Duration (d, w, m) [1] | 1 d | 3 d | 1 w | 2 w | 1 m | 2 m | 3 m | 4 m | 5 m |
| $C_6H_4(CH_3)_2$ | ■ | ■ | ■ | ■ | ■ | ■ | ■ | ■ | ■ |
| $C_2H_5OH$ 95% | ■ | ■ | ■ | ■ | ■ | ■ | ■ | ■ | ■ |
| $CH_3COOH$ 10% | ▫ | ▫ | ▫ | ▫ | ▫ | ▫ | ▫ | ▫ | ▫ |
| $CH_3COOH$ 5% | ⌘ | ⌘ | ▫ | ▫ | ▫ | ▫ | ▫ | ▫ | ▫ |

| Duration (d, w, m) [1] | 6 m | 7 m | 8 m | 9 m | 10 m | 11 m | 12 m |
|---|---|---|---|---|---|---|---|
| $C_6H_4(CH_3)_2$ | ■ | ■ | ■ | ■ | ■ | ■ | ■ |
| $C_2H_5OH$ 95% | ■ | ■ | ■ | ■ | ■ | ■ | ■ |
| $CH_3COOH$ 10% | ▫ | ▫ | ▫ | ▫ | ▫ | ▫ | ▫ |
| $CH_3COOH$ 5% | ▫ | ▫ | ▫ | ▫ | ▫ | ▫ | ▫ |

For tables 10 to 17:
[1] d, w, m = days, weeks, months;
coating surface is either ■ = resistant to, ⌘ = attacked by, or ▫ = destroyed by the chemical

TABLE 11

Chemical resistance of the neat system TMD/Araldite GY250 (unmodified system)

| Epoxid/Hardener | Araldite GY250: TMD: | | | | 82.32 parts/ 17.68 parts | | | | |
|---|---|---|---|---|---|---|---|---|---|
| Duration (d, w, m) [1] | 1 d | 3 d | 1 w | 2 w | 1 m | 2 m | 3 m | 4 m | 5 m |
| $C_6H_4(CH_3)_2$ | ■ | ■ | ■ | ■ | ■ | ■ | ■ | ■ | ■ |
| $C_2H_5OH$ 95% | ■ | ■ | ■ | ⌘ | ⌘ | ⌘ | ⌘ | ⌘ | ⌘ |
| $CH_3COOH$ 10% | ⌘ | ⌘ | ▫ | ▫ | ▫ | ▫ | ▫ | ▫ | ▫ |
| $CH_3COOH$ 5% | ⌘ | ⌘ | ⌘ | ⌘ | ⌘ | ▫ | ▫ | ▫ | ▫ |

| Duration (d, w, m) [1] | 6 m | 7 m | 8 m | 9 m | 10 m | 11 m | 12 m |
|---|---|---|---|---|---|---|---|
| $C_6H_4(CH_3)_2$ | ■ | ■ | ■ | ■ | ■ | ■ | ■ |
| $C_2H_5OH$ 95% | ⌘ | ⌘ | ⌘ | ⌘ | ⌘ | ⌘ | ⌘ |
| $CH_3COOH$ 10% | ▫ | ▫ | ▫ | ▫ | ▫ | ▫ | ▫ |
| $CH_3COOH$ 5% | ▫ | ▫ | ▫ | ▫ | ▫ | ▫ | ▫ |

The chemical resistance of coatings made with the above amines containing Supraplast 3616 of about 25 wt %, the upper limit that is mentioned in the patent WO 99/29757, is given in tables 12 and 13. The chemical resistance is improved a little bit if compared with the neat systems in both cases of TMD and MXDA, but the coatings are attacked or destroyed in a short time in the case of an aggressive chemical in the form of an aqueous solution of 10 wt % acetic acid.

TABLE 12

Chemical resistance of MXDA containing 25 wt % novolac resin Supraplast 3616

| Epoxid/ | Araldite GY250: | 80.43 p./ |
|---|---|---|
| Hardener | MXDA/Supraplast 75/25: | 19.57 p. |

TABLE 12-continued

Chemical resistance of MXDA containing 25 wt % novolac resin Supraplast 3616

| Duration (d, w, m) | 1 d | 3 d | 1 w | 2 w | 1 m | 2 m | 3 m | 4 m | 5 m |
|---|---|---|---|---|---|---|---|---|---|
| $C_6H_4(CH_3)_2$ | ■ | ■ | ■ | ■ | ■ | ■ | ■ | ■ | ■ |
| $C_2H_5OH$ 95% | ■ | ■ | ■ | ■ | ■ | ■ | ■ | ■ | ■ |
| $CH_3COOH$ 10% | ■ | ■ | ⌘ | ⌘ | ⌘ | □ | □ | □ | □ |
| $CH_3COOH$ 5% | ■ | ■ | ■ | ■ | ■ | ■ | ■ | ■ | ■ |

| Duration (d, w, m) | 6 m | 7 m | 8 m | 9 m | 10 m | 11 m | 12 m |
|---|---|---|---|---|---|---|---|
| $C_6H_4(CH_3)_2$ | ■ | ■ | ■ | ■ | ■ | ■ | ■ |
| $C_2H_5OH$ 95% | ■ | ■ | ■ | ■ | ■ | ■ | ■ |
| $CH_3COOH$ 10% | □ | □ | □ | □ | □ | □ | □ |
| $CH_3COOH$ 5% | ■ | ■ | ■ | ■ | ■ | ■ | ■ |

TABLE 13

Chemical resistance of TMD containing 25 wt % novolac resin Supraplast 3616

| Epoxid/Hardener | Araldite GY250: 77.74 p./ TMD/Supraplast 75/25: 22.26 p. | | | | | | | | |
|---|---|---|---|---|---|---|---|---|---|
| Duration (d, w, m) | 1 d | 3 d | 1 w | 2 w | 1 m | 2 m | 3 m | 4 m | 5 m |
| $C_6H_4(CH_3)_2$ | ■ | ■ | ■ | ■ | ■ | ■ | ■ | ■ | ■ |
| $C_2H_5OH$ 95% | ⌘ | ⌘ | ⌘ | ⌘ | ⌘ | ⌘ | ⌘ | ⌘ | ⌘ |
| $CH_3COOH$ 10% | ⌘ | ⌘ | ⌘ | □ | □ | □ | □ | □ | □ |
| $CH_3COOH$ 5% | ⌘ | ⌘ | ⌘ | ⌘ | ⌘ | ⌘ | ⌘ | ⌘ | ⌘ |

| Duration (d, w, m) | 6 m | 7 m | 8 m | 9 m | 10 m | 11 m | 12 m |
|---|---|---|---|---|---|---|---|
| $C_6H_4(CH_3)_2$ | ■ | ■ | ■ | ■ | ■ | ■ | ■ |
| $C_2H_5OH$ 95% | ⌘ | ⌘ | ⌘ | ⌘ | ⌘ | ⌘ | ⌘ |
| $CH_3COOH$ 10% | □ | □ | □ | □ | □ | □ | □ |
| $CH_3COOH$ 5% | ⌘ | ⌘ | ⌘ | ⌘ | ⌘ | ⌘ | ⌘ |

The chemical resistance of the inventive hybrid compositions containing high amounts of Supraplast 3616 is given for both cases of MXDA and TMD respectively in tables 14 and 15 below. The resistance of the coatings is improved especially in the case of TMD hardener for which the resistance toward an aqueous solution of acetic acid at 5 wt % passes 7 months and is only a little attacked by an aqueous solution acetic acid 5 wt % after 12 months exposure. Also the time of resistance toward the very aggressive chemical in the form of an aqueous solution of acetic acid 10 wt % is prolonged in both cases for a couple of months.

TABLE 14

Chemical resistance of MXDA containing 41 wt % novolac resin Supraplast 3616

| Epoxid/Hardener | Araldite GY250: 76.36 p./ MXDA/Supraplast 59/41: 23.64 p. | | | | | | | | |
|---|---|---|---|---|---|---|---|---|---|
| Duration (d, w, m) | 1 d | 3 d | 1 w | 2 w | 1 m | 2 m | 3 m | 4 m | 5 m |
| $C_6H_4(CH_3)_2$ | ■ | ■ | ■ | ■ | ■ | ■ | ■ | ■ | ■ |
| $C_2H_5OH$ 95% | ■ | ■ | ■ | ■ | ■ | ■ | ■ | ■ | ■ |
| $CH_3COOH$ 10% | ■ | ■ | ■ | ■ | ■ | ■ | ⌘ | □ | □ |
| $CH_3COOH$ 5% | ■ | ■ | ■ | ■ | ■ | ■ | ■ | ■ | ■ |

| Duration (d, w, m) | 6 m | 7 m | 8 m | 9 m | 10 m | 11 m | 12 m |
|---|---|---|---|---|---|---|---|
| $C_6H_4(CH_3)_2$ | ■ | ■ | ■ | ■ | ■ | ■ | ■ |
| $C_2H_5OH$ 95% | ■ | ■ | ■ | ■ | ■ | ■ | ■ |
| $CH_3COOH$ 10% | □ | □ | □ | □ | □ | □ | □ |
| $CH_3COOH$ 5% | ■ | ■ | ■ | ■ | ■ | ■ | ■ |

TABLE 15

Chemical resistance of TMD containing 40 wt % novolac resin Supraplast 3616

| Epoxid/ | Araldite GY250: | | | | | | 73.64 p./ | | | |
|---|---|---|---|---|---|---|---|---|---|---|
| Hardener | TMD/Supraplast 3616 60/40: | | | | | | 26.36 p. | | | |
| Duration (d, w, m) | 1 d | 3 d | 1 w | 2 w | 1 m | 2 m | 3 m | 4 m | 5 m | 6 m |
| $C_6H_4(CH_3)_2$ | ■ | ■ | ■ | ■ | ■ | ■ | ■ | ■ | ■ | ■ |
| $C_2H_5OH$ 95% | ■ | ■ | ■ | ■ | ■ | ⌘ | ⌘ | ⌘ | ⌘ | ⌘ |
| $CH_3COOH$ 10% | ■ | ■ | ■ | ■ | ■ | ■ | ⌘ | ⌘ | □ | ■ |
| $CH_3COOH$ 5% | ■ | ■ | ■ | ■ | ■ | ■ | ■ | ■ | ■ | ■ |

| Duration (d, w, m) | 7 m | 8 m | 9 m | 10 m | 11 m | 12 m |
|---|---|---|---|---|---|---|
| $C_6H_4(CH_3)_2$ | ■ | ■ | ■ | ■ | ■ | ■ |
| $C_2H_5OH$ 95% | ⌘ | ⌘ | ⌘ | ⌘ | ⌘ | ⌘ |
| $CH_3COOH$ 10% | | | | | | |
| $CH_3COOH$ 5% | ■ | ⌘ | ⌘ | ⌘ | ⌘ | ⌘ |

The results with regard to the chemical resistance of a system cured with an inventive hybrid hardener blend further modified by the addition of minor amounts of 1 or 2 wt % of salicylic acid are given in the following tables 16 and 17. The obtained results of chemical resistance toward aqueous acetic acid 10 wt % are surprisingly exceptionally good. Said modified system shows a real improvement of the resistance toward such a chemical, which was only possible until now with a mixture of aromatic amines based on diaminodiphenylmethane (DDM):

TABLE 16

Chemical resistance of hybrid hardener composed of 62.37 wt % MXDA, 36.63 wt % novolac resin Supraplast 3616 and 1 wt % salicylic acid.

| Epoxid/ | Araldite GY250: | | | | | | | | 79.14 p./ | | | | | | |
|---|---|---|---|---|---|---|---|---|---|---|---|---|---|---|---|
| Hardener | MXDA/Supraplast/salicylic acid: 62.37/36.63/1.00: | | | | | | | | 20.86 p. | | | | | | |
| Duration (d, w, m) | 1 d | 3 d | 1 w | 2 w | 1 m | 2 m | 3 m | 4 m | 5 m | 6 m | 7 m | 8 m | 9 m | 10 m | 11 m 12 m |
| $C_6H_4(CH_3)_2$ | ■ | ■ | ■ | ■ | ■ | ■ | ■ | ■ | ■ | ■ | ■ | ■ | ■ | under evaluation | |
| $C_2H_5OH$ 95% | ■ | ■ | ■ | ■ | ■ | ■ | ■ | ■ | ■ | ■ | ■ | ■ | ■ | under evaluation | |
| $CH_3COOH$ 10% | ■ | ■ | ■ | ■ | ■ | ■ | ■ | ■ | ■ | ■ | ■ | ■ | ■ | under evaluation | |
| $CH_3COOH$ 5% | ■ | ■ | ■ | ■ | ■ | ■ | ■ | ■ | ■ | ■ | ■ | ■ | ■ | under evaluation | |

TABLE 17

Chemical resistance of hybrid hardener composed of 62.37 wt % MXDA, 36.63 wt % novolac resin Supraplast 3616 and 2 wt % salicylic acid.

| Epoxid/ | Araldite GY250: | | | | | | | | 78.71 p./ | | | | | | |
|---|---|---|---|---|---|---|---|---|---|---|---|---|---|---|---|
| Hardener | MXDA/Supraplast/salicylic acid: 60.76/37.24/2.00: | | | | | | | | 21.29 p. | | | | | | |
| Duration (d, w, m) | 1 d | 3 d | 1 w | 2 w | 1 m | 2 m | 3 m | 4 m | 5 m | 6 m | 7 m | 8 m | 9 m | 10 m | 11 m 12 m |
| $C_6H_4(CH_3)_2$ | ■ | ■ | ■ | ■ | ■ | ■ | ■ | ■ | ■ | ■ | ■ | ■ | ■ | under evaluation | |
| $C_2H_5OH$ 95% | ■ | ■ | ■ | ■ | ■ | ■ | ■ | ■ | ■ | ■ | ■ | ■ | ■ | under evaluation | |
| $CH_3COOH$ 10% | ■ | ■ | ■ | ■ | ■ | ■ | ■ | ■ | ■ | ■ | ■ | ■ | ■ | under evaluation | |
| $CH_3COOH$ 5% | ■ | ■ | ■ | ■ | ■ | ■ | ■ | ■ | ■ | ■ | ■ | ■ | ■ | under evaluation | |

F) Corrosion Resistance of a Hybrid System Based on TMD/Supraplast 3616

The corrosion resistance was measured following DIN 35167 and DIN 50021-SS, the salt spray test. The hybrid hardener C [TMD/Supraplast 60/40] of table 1 was formulated as an anticorrosive primer as given in table 18 and applied with a spray gun on sand blasted steel panels Sa $2^{1/2}$ 100 mm×70 mm at thicknesses of 160 μm and 80 μm. The coated panels were allowed to cure during 7 days at 23° C./50% rh. After this time, the coated panels were scribed in X-shape with the Scratch Stylus 463 from Erichsen, each leg being approximately 5 cm in length. The panels were then exposed to salt spray during different times for instance 500 h, 1000 h, 2000 h and 4000 h.

TABLE 18

Anticorrosive primer formulation using hardener C

| Primer formulation epoxy/hybrid hardener | Parts by weight |
|---|---|
| GY 250 | 85.1 |
| Luvotix P 25 X (thickener) | 8.1 |
| ZP 10 (Zinc phosphate) | 22.5 |

TABLE 18-continued

Anticorrosive primer formulation using hardener C

| Primer formulation epoxy/hybrid hardener | Parts by weight |
|---|---|
| Talc 10 MO | 75.3 |
| Iron oxide 130 | 14.85 |
| BaSO₄ EWO S | 30.1 |
| Xylene-butanol 4:1 | 69.5 |
| Hardener C | 30.4 |

Luvotix P 25 X is a thixotropic agent (Lehmann&Voss&Co);
Zinc phosphate ZP 10 (Heubach GmbH)
Talc 10 MO (Talc de Luzenac France);
Barium sulfate EWO ®-S (Sachtleben Chemie GmbH)
Iron oxide red 130 (BAYER);
Hardener C (see table 1)

The results of the corrosion test for the primer formulation using the hybrid hardener C (see table 1) are given in table 19 below. The value $W_A$ in formula (III) depends on the undercoat corrosion area created during the exposure time. The higher this value becomes, the worse is the corrosion resistance of the coating. In the present case, minimal undercoat corrosion was observed during an exposure time of almost 4000 h.

$$W_A = \frac{A_1 - A_0}{2} \cdot \frac{1}{L} \quad \text{Formula (III)}$$

$A_1$=Total surface of the under corrosion zone in mm²;
$A_0$=Surface of the scrubbed line in mm²;
L=Length of the scrubbed line in mm

TABLE 19

$W_A$ value obtained at different corrosion times for the hybrid hardener C in table 1

| System | Exposure time | | | |
|---|---|---|---|---|
| | 500 h | 1000 h | 2000 h | 4000 h |
| $W_A$ for TMD/Supraplast [60/40] 80 µm | 0 | 7 | 8 | 16 |
| $W_A$ for TMD/Supraplast [60/40] 160 µm | 1 | 13 | 15 | 16 |
| Corroded surface in mm² for MD/Supraplast [60/40] 80 µm | 0 | 153 | 177 | 337 |
| Corroded surface in mm² for MD/Supraplast [60/40] 160 µm | 30 | 261 | 310 | 334 |

$A_0$=Surface of the scrubbed line in mm²=10×1 mm²
L=Length of the scrubbed line in mm=10 mm The coatings made with such hybrid hardener based on TMD show subsequently excellent resistance to corrosion with minimal undercoat corrosion and can for instance be further used in marine primer formulation.

What is claimed is:

1. A curable composition comprising:
   a) an epoxy resin containing on average more than one epoxy group per molecule; and
   b) as curing agent, a hybrid hardener;
   wherein said hybrid hardener is a blend of b1) and b2):
      b1) an aminic compound selected from the group consisting of aliphatic amines, cycloaliphatic amines, araliphatic amines, imidazoline group-containing amidoamines based on mono- or polybasic acids, adducts of said amines or amidoamines and glycidyl compounds, and adducts of said amines or amidoamines and cyclic carbonates, wherein said aminic compound contains, on average per molecule, at least two reactive hydrogen atoms bound to nitrogen atoms; and
      b2) a polyphenol novolac, wherein the polyphenol novolac is present in an amount of from 30% to 45% by weight, based on the total weight of the blend of b1) and b2);
   wherein the hybrid hardener is a liquid having a viscosity lower than 20,000 mPa·s at a temperature of 20±5° C.; and
   wherein the curable composition is a protective coating curable at a temperature of from about −5° C. to about 50° C.

2. The composition according to claim 1, wherein the polyphenol novolac is present in an amount of from 35% to 45% by weight, based on the total weight of the blend of b1) and b2).

3. The composition according to claim 1, wherein the polyphenol novolac is a homopolymer resulting from the condensation of phenolic compounds of formula (I) or (II) with formaldehyde or paraformaldehyde or a copolymer of different phenolic compounds of formula (I) and/or (II) with formaldehyde or paraformaldehyde:

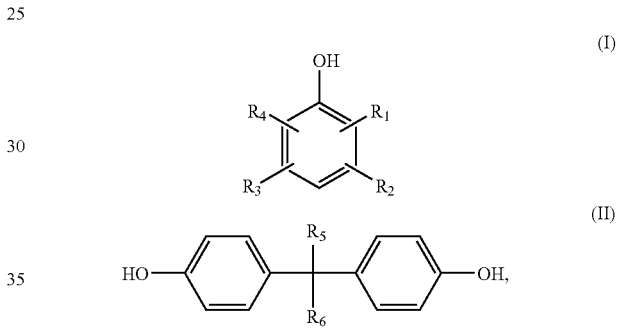

wherein in formula (I) and (II) $R_1$, $R_2$, $R_3$, $R_4$, independently of one another are H, branched or unbranched alkyl radicals containing 1 to 15 carbon atoms, and $R_5$, $R_6$ independently of each other represent H, $CH_3$ or $CF_3$.

4. The composition according to claim 1, wherein the polyphenol novolac comprises unreacted free phenolic compounds in an amount of no more than 20% by weight, based on the total weight of the blend of b1) and b2).

5. The composition according claim 1, wherein b1) is selected from the group consisting of aliphatic amines, cycloaliphatic amines, and araliphatic amines.

6. The composition according to claim 5, wherein b1) is selected from the group consisting of m-xylylenediamine, isophoronediamine, trimethylhexamethylenediamine, 1,2-diaminocyclohexane, 1,3-bis(aminomethyl)cyclohexane, diethylenetriamine, and diaminodicyclohexyl methane.

7. The composition according to claim 1, wherein the cyclic carbonate is selected from the group consisting of ethylene carbonate, 1,2-propylene carbonate and 1,2-butylenecarbonate.

8. The composition according to claim 1, wherein component a) is selected from the group consisting of diglycidylether of bisphenol A, diglycidylether of bisphenol F, polyglycidylether of polyhydric phenol or cresol novolacs, polyglycidylether of polyhydric cycloaliphatic alcohols, and polyglycidylether of polyhydric aliphatic alcohols.

9. The composition according to claim 1 further comprising a reactive diluent, wherein component a) is premixed with the reactive diluent.

10. The composition according to claim 1 further comprising a cyclic carbonate, wherein component a) is premixed with the cyclic carbonate.

11. The composition according to claim 1 further comprising an inorganic additive, an organic additive or combinations thereof, wherein the additives are selected from the group consisting of flow control additives, antifoaming agents, antisag agents, pigments, reinforcing agents, fillers, elastomers, stabilizers, extenders, plasticizers, flame retardants, accelerators, colorants, fibrous substances, thixotropic agents, anticorrosive pigments and solvents.

12. The composition according to claim 11, wherein the organic additive is salicylic acid.

13. A cured material obtained by curing the composition according to claim 1.

14. A process for improving the corrosion resistance of a substrate comprising: applying the curable composition according to claim 1 to at least one surface of the substrate; and curing the composition.

15. A hybrid hardener, wherein the hybrid hardener is a blend of b1) and b2):
- b1) an aminic compound selected from the group consisting of aliphatic amines, cycloaliphatic amines, araliphatic amines, imidazoline group-containing amidoamines based on mono- or polybasic acids, adducts of said amines or amidoamines and glycidyl compounds, and adducts of said amines or amidoamines and cyclic carbonates, wherein said aminic compound contains, on average per molecule, at least two reactive hydrogen atoms bound to nitrogen atoms; and
- b2) a polyphenol novolac, wherein the polyphenol novolac is present in an amount of from 30% to 45% by weight, based on the total weight of b1) and b2);
- wherein the hybrid hardener is a liquid having a viscosity lower than 20,000 mPa·s at a temperature of 20±5° C.

* * * * *